(12) United States Patent
Hata et al.

(10) Patent No.: US 11,096,552 B2
(45) Date of Patent: Aug. 24, 2021

(54) METHOD AND APPARATUS FOR CONTROLLING MANIPULATOR

(71) Applicants: CANON U.S.A., INC., Melville, NY (US); THE BRIGHAM AND WOMEN'S HOSPITAL INC., Boston, MA (US); Nobuhiko Hata, Newton, MA (US); Takahisa Kato, Brookline, MA (US); Kiyoshi Takagi, Tokyo (JP); Hidekazu Kose, Tokyo (JP)

(72) Inventors: Nobuhiko Hata, Newton, MA (US); Takahisa Kato, Brookline, MA (US); Kiyoshi Takagi, Tokyo (JP); Hidekazu Kose, Tokyo (JP)

(73) Assignees: Canon U.S.A., Inc., Melville, NY (US); The Brigham and Women's Hospital Inc., Boston, MA (US)

( * ) Notice: Subject to any disclaimer, the term of this patent is extended or adjusted under 35 U.S.C. 154(b) by 445 days.

(21) Appl. No.: 15/741,171

(22) PCT Filed: Jun. 30, 2015

(86) PCT No.: PCT/US2015/038662
§ 371 (c)(1),
(2) Date: Dec. 29, 2017

(87) PCT Pub. No.: WO2017/003468
PCT Pub. Date: Jan. 5, 2017

(65) Prior Publication Data
US 2018/0192854 A1 Jul. 12, 2018

(51) Int. Cl.
| | | |
|---|---|---|
| *A61B 1/00* | (2006.01) |
| *A61B 1/005* | (2006.01) |
| *B25J 9/16* | (2006.01) |
| *A61B 34/30* | (2016.01) |
| *A61B 1/018* | (2006.01) |
| *B25J 9/10* | (2006.01) |
| *B25J 13/06* | (2006.01) |
| *B25J 18/06* | (2006.01) |

(52) U.S. Cl.
CPC ........ *A61B 1/00006* (2013.01); *A61B 1/0016* (2013.01); *A61B 1/0051* (2013.01);
(Continued)

(58) Field of Classification Search
CPC ............ A61B 1/00006; A61B 1/00147; A61B 1/0057; A61B 34/37
(Continued)

(56) References Cited

U.S. PATENT DOCUMENTS

2003/0125716 A1* 7/2003 Wang ..................... A61B 17/11
606/1
2004/0193015 A1 9/2004 Ikeda et al.
(Continued)

FOREIGN PATENT DOCUMENTS

EP 2070465 A1 6/2009
JP H08196541 A 8/1996
(Continued)

*Primary Examiner* — Alexandra L Newton
*Assistant Examiner* — Rynae Boler
(74) *Attorney, Agent, or Firm* — Canon U.S.A., Inc. IP Division

(57) ABSTRACT

The present invention provides a method and an apparatus for controlling a flexible manipulator including a plurality of bendable mechanisms via a control apparatus. The control apparatus includes a drive-mode selecting unit allows for the selection of a movement mode which may provide a bending movement, an angled view movement, or a remote center movement.

15 Claims, 10 Drawing Sheets

(52) U.S. Cl.
 CPC ........ *A61B 1/0057* (2013.01); *A61B 1/00183* (2013.01); *A61B 1/018* (2013.01); *A61B 34/30* (2016.02); *B25J 9/104* (2013.01); *B25J 9/1635* (2013.01); *B25J 13/065* (2013.01); *B25J 18/06* (2013.01); *A61B 2034/301* (2016.02); *G05B 2219/49253* (2013.01)

(58) Field of Classification Search
 USPC .......................................................... 600/106
 See application file for complete search history.

(56) References Cited

U.S. PATENT DOCUMENTS

| | | | | |
|---|---|---|---|---|
| 2011/0257480 | A1* | 10/2011 | Takahashi | A61B 1/00147 600/106 |
| 2015/0164596 | A1* | 6/2015 | Romo | A61M 25/0012 604/104 |
| 2016/0135909 | A1* | 5/2016 | Ogawa | A61B 34/37 606/130 |
| 2017/0360519 | A1* | 12/2017 | Yorimoto | A61B 1/00039 |

FOREIGN PATENT DOCUMENTS

| | | |
|---|---|---|
| JP | 2001137257 A | 5/2001 |
| JP | 2001286437 A | 10/2001 |
| JP | 2006116289 A | 5/2006 |
| WO | 2011058893 A1 | 3/2013 |
| WO | 2011114568 A1 | 6/2013 |
| WO | 2015/012142 A1 | 1/2015 |
| WO | 2015012162 A1 | 1/2015 |

\* cited by examiner (a)          (b)          (c)

Fig. 12
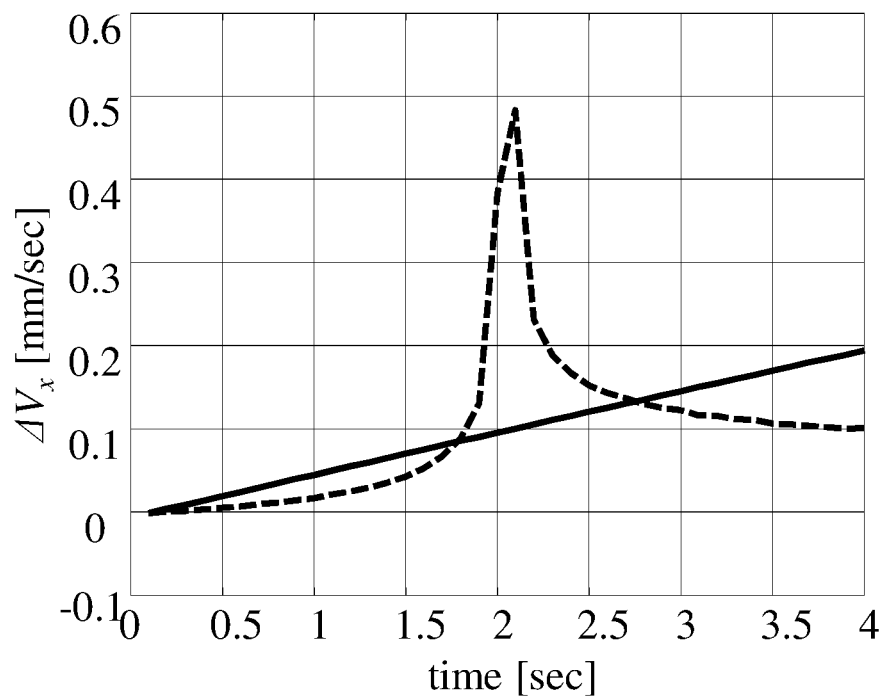
Figs. 13(a) – 13(b)
(a) 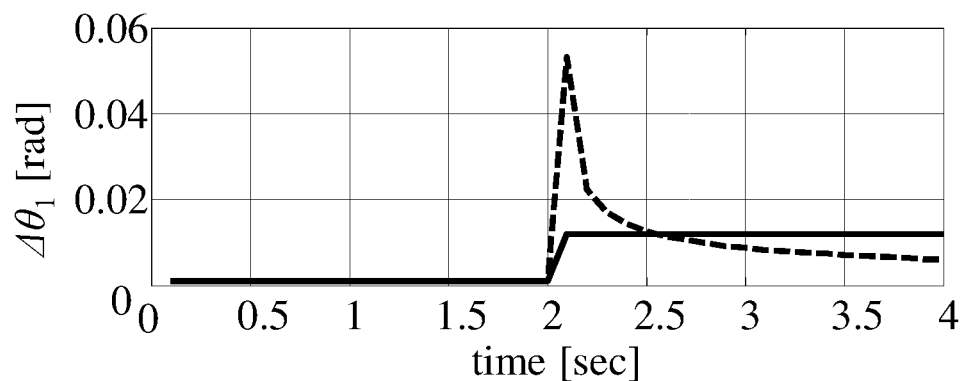
(b) 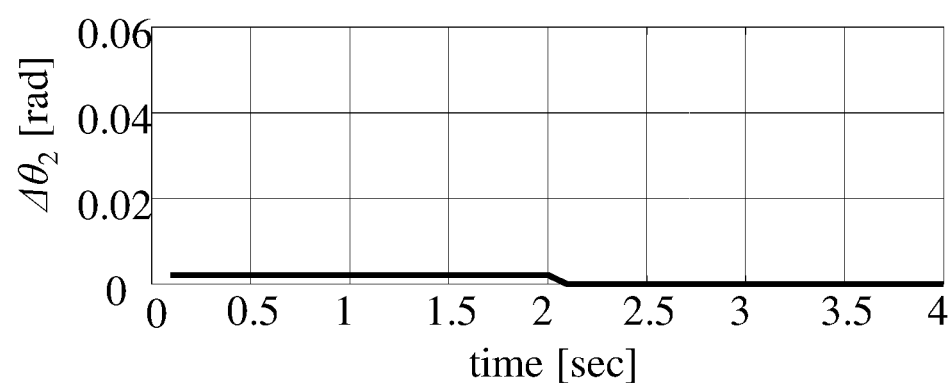

METHOD AND APPARATUS FOR CONTROLLING MANIPULATOR

BACKGROUND OF THE INVENTION

Field of the Invention

The present invention relates to a method and an apparatus for controlling a flexible manipulator including a plurality of bendable mechanisms.

Description of the Related Art

In recent years, minimally invasive medical care, with which burden on the patient can be reduced and the quality of life (QOL) after the treatment or inspection can be improved, has been attracting attention. A surgery or inspection using an endoscope is a typical example of minimally invasive medical care. For example, a laparoscopic surgery is advantageous over a conventional abdominal surgery in that it can be performed with a smaller surgical wound, which results in a shorter stay in the hospital and less damage to the appearance.

Endoscopes used for the minimally invasive medical care are roughly divided into rigid endoscopes and soft endoscopes. With a rigid endoscope, although clear images can be obtained, the direction in which an observation target can be observed is limited. In addition, when the rigid endoscope is inserted into a curved organ, such as the esophagus, large intestine, or urethra, an insertion portion of the rigid endoscope presses the organ and causes pain for the patient. In contrast, a soft endoscope includes an insertion portion formed of a bendable member, so that a large area can be observed in detail by adjusting the bending angle of the distal end of the endoscope. In addition, by bending the insertion portion along an insertion path, burden on the patient can be reduced. When the number of bendable portions is increased, the endoscope can be inserted to a deep area of the body without causing the endoscope to come into contact with tissue even when the insertion path has a complex curved shape. Accordingly, soft endoscopes having a plurality of bendable portions have been widely researched and developed.

The inspection and surgery using an endoscope have a problem that operation of the endoscope requires skill. One reason for this is that the physician cannot directly observe the position of the insertion portion of the endoscope, and the relationship between the operating direction and the direction of movement in the observed image cannot be easily recognized. In particular, when the number of bendable portions is increased, the position of the insertion portion varies in a complex manner, and therefore the difficulty of operation is further increased. As a result, the time required for the inspection or surgery is increased, and burden on the physician and the patient is increased accordingly.

When a camera for observation in both an axial direction and a radial direction is mounted on the insertion portion, as described in Japanese Patent Laid-Open No. 12010-12079, the surface of the insertion path can be observed without operating the bendable portions.

However, with the endoscope according to Japanese Patent Laid-Open No. 2010-12079, since the camera is fixed to the insertion portion, the bendable portions still need to be operated to change the direction of observation to a desired direction. Therefore, to realize an endoscope with which a large area can be easily observed, it is desirable to improve the operability of the endoscope.

SUMMARY OF THE INVENTION

According to an aspect of the present invention, a control apparatus for a manipulator including a plurality of bendable portions includes a plurality of driving-force transmitting mechanisms that are connected to the bendable portions and that bend the manipulator; a plurality of drive sources that apply drive forces to the driving-force transmitting mechanisms; an operation-amount input unit that generates an operation signal based on an amount of operation of an operating portion; a movement-mode input unit that selects one of a plurality of movement modes; and a calculating device that calculates and outputs driving amounts to be applied to the drive sources on the basis of the operation signal, the driving amounts corresponding to the movement modes. The calculating device includes a plurality of driving-amount calculators, and a movement-mode selecting unit that outputs the driving amounts output by one of the driving-amount calculators on the basis of an input signal from the a movement-mode input unit.

According to this aspect of the present invention, an operator selects a movement pattern that matches the purpose of inspection or surgery from among a plurality of movement patterns that are set in advance, and the control apparatus calculates the driving amounts required to realize the selected movement pattern. Accordingly, the operator needs only to perform a simple operation to carry out the selected movement.

In the control apparatus, one of the driving-amount calculators may calculate the driving amounts so that the bendable portions are bent in the same direction.

In this case, since the distal end of the manipulator is moved by a large amount, observation can be performed over a wide area.

The one of the driving-amount calculators may include a plurality of first amplifiers that calculate the driving amounts by amplifying the operation signal.

In this case, even when the position of the manipulator cannot be precisely measured or predicted, variation in the movement speed of the distal end of the manipulator can be reduced.

In the control apparatus, one of the driving-amount calculators may calculate the driving amounts such that an angle of a distal end of at least one of the bendable portions is constant.

In this case, observation along a wall surface can be performed.

The one of the driving-amount calculators may include a second amplifier that calculates a corresponding one of the driving amounts by amplifying the operation signal. The second amplifier may correspond to the at least one of the bendable portions having the distal end whose angle is constant, and an amplification factor of the second amplifier may be set to zero.

In this case, even when the position of the manipulator cannot be precisely measured or predicted, variation in the movement speed of the distal end of the manipulator can be reduced.

In the control apparatus, one of the driving-amount calculators may receive observation-target coordinates and calculate the driving amounts such that a straight line that extends in a longitudinal direction from the most distal bendable portion of the manipulator passes through a position specified by the coordinates.

In this case, a portion that cannot be viewed from the front side of the manipulator can be observed.

The one of the driving-amount calculators may include a plurality of third amplifiers that calculate the driving amounts by amplifying the operation signal, and a storage section that receives a signal of the observation-target coordinates and outputs third amplification factors of the third amplifiers. The driving amounts may be calculated by amplifying the operation signal by the third amplification.

In this case, even when the position of the manipulator cannot be precisely measured or predicted, variation in the movement speed of the distal end of the manipulator can be reduced.

Further features of the present invention will become apparent from the following description of exemplary embodiments with reference to the attached drawings.

BRIEF DESCRIPTION OF THE DRAWINGS

FIG. 12 is a graph showing a simulation result according to the second embodiment.

FIGS. 13(a) and 13(b) are graphs showing a simulation result according to the second embodiment.

DESCRIPTION OF THE EMBODIMENTS

First Embodiment 1-1 Structure of Apparatus

Figure 1:
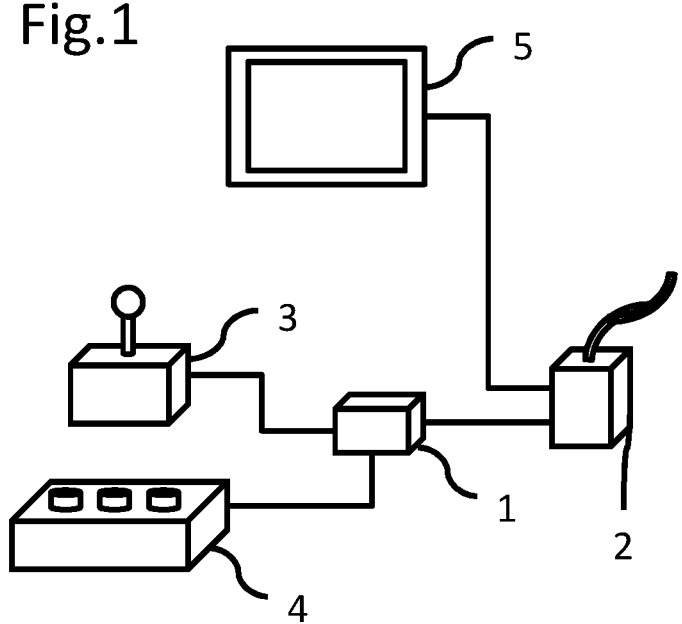
FIG. 1 is a schematic diagram illustrating a manipulator operation system according to an embodiment of the present invention.

A control apparatus according to a first embodiment of the present invention is applied to a wire-driven manipulator including two bendable portions. FIG. 1 is a schematic diagram of a manipulator operation system. FIG. 1 illustrates a control apparatus 1 according to the first embodiment of the present invention, a bending manipulator 2, an operation-amount input unit 3, a movement-mode input unit 4, and an image display device 5. In this exemplary embodiment, the movement-mode input unit 4 includes three push switches, and outputs a movement mode signal when any of the push switches is pressed. The operation-amount input unit 3 includes a single-axis joystick, and outputs an operation input $\Delta m$ in accordance with the amount of operation of the joystick. The control apparatus 1 selects, on the basis of the movement mode signal, one of three types of movement patterns that are set in advance. Then, the control apparatus 1 calculates driving amounts $\Delta \theta_1$ and $\Delta \theta_2$ to be input to drive sources of the bending manipulator 2 on the basis of the operation input $\Delta m$.

In some embodiments, the operation-amount input unit 3 is a slide bar, a touch screen, a non-contact input unit (e.g., a doctor can move a finger left to right to control input) or other input device allowing for input of an input used to generate an operation signal. Similarly, the movement-mode input unit may be a single toggle switch with three positions, a foot pedal, a touch screen with three mode choices, etc. In other embodiments, the control apparatus may comprise a movement-mode input unit allowing for the selection of 2, 3, 4, or more modes instead of the three modes exemplified above.

Figure 2:
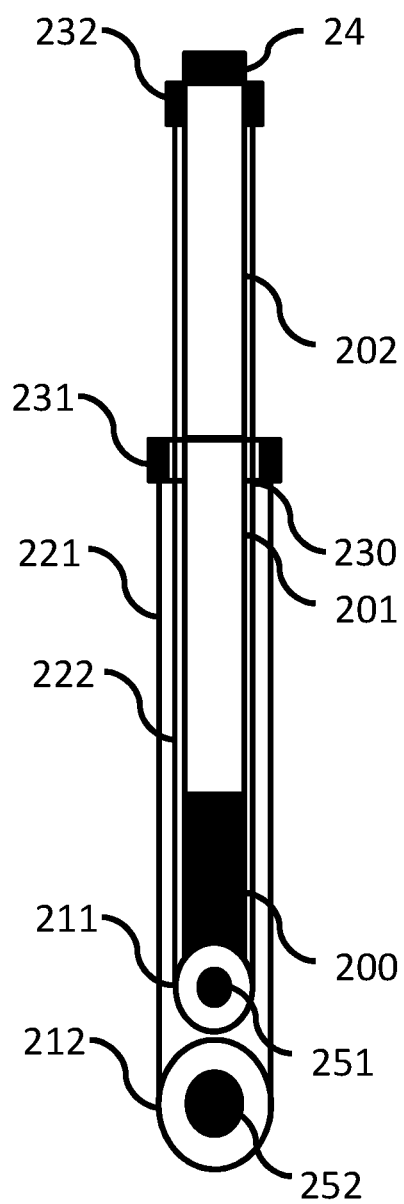
FIG. 2 is a schematic diagram illustrating a wire-driven manipulator including a plurality of bendable portions.

FIG. 2 illustrates the structure of the bending manipulator 2. The bending manipulator 2 includes an insertion portion and drive sources 211 and 212 that apply driving forces to the insertion portion. The insertion portion includes a rigid portion 200 formed of a material having a high rigidity and bendable portions formed of flexible materials. The bendable portions include a first bendable portion 201 provided at a proximal side and a second bendable portion 202 provided at a distal side. The rigid portion 200 and the bendable portions 201 and 202 have a hollow structure, and are therefore capable of guiding a forceps, a cleaning device, a camera, a cutting tool, etc. there through.

A wire 221, which functions as a driving-force transmitting mechanism, has one end fixed to a wire-fixing portion 231 of the first bendable portion, and is wound around an output shaft of the drive source 212. Therefore, when the drive source 212 is rotated, the wire 221 is pulled and the first bendable portion 201 is bent. Similarly, a wire 222 extends through a wire guide 230, and is fixed to a wire-fixing portion 232 provided at an end of the second bendable portion. In addition, the wire 222 is wound around the drive source 211, so that when the source 211 is driven, the second bendable portion 202 is bent.

Figure 3:
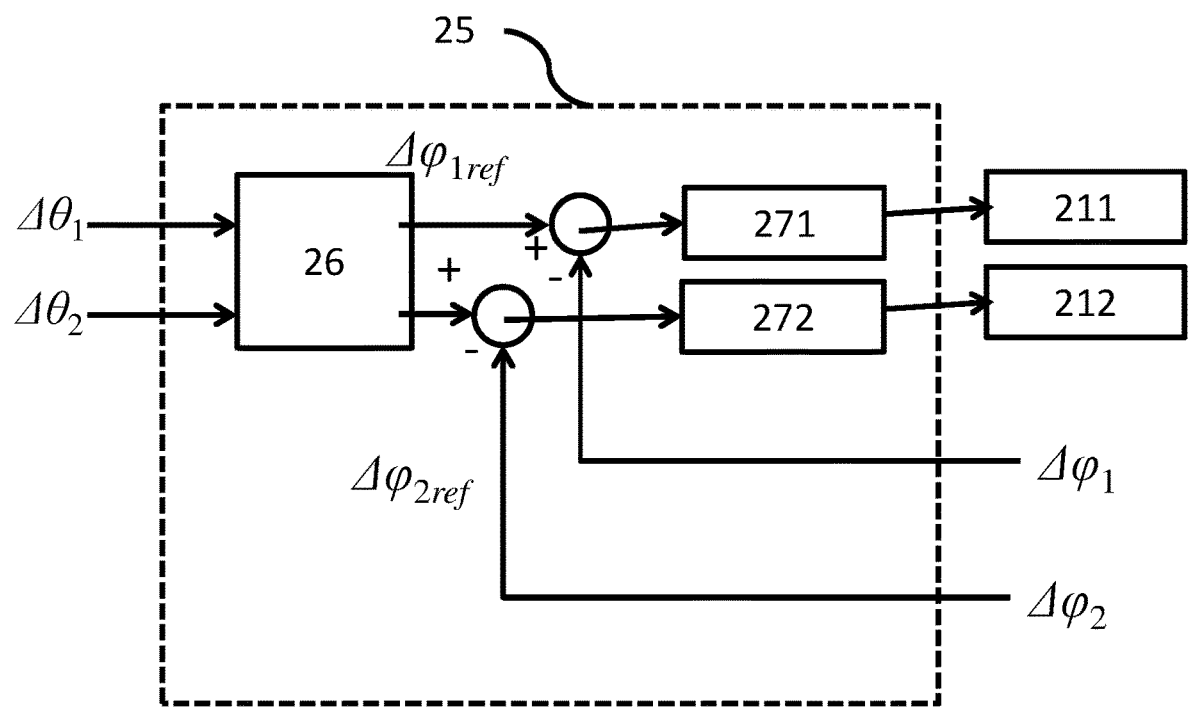
FIG. 3 is a block diagram of a position control apparatus for drive sources.

The drive sources 211 and 212 are provided with encoders 251 and 252 that detect rotational angles of the drive sources 211 and 212, and a position control apparatus 25 (not shown) that controls the rotational angles. The position control apparatus 25 controls the rotational angles of the drive sources 211 and 212 so as to increase or reduce the angles $\theta_1$ and $\theta_2$ of the distal ends of the first and second bendable portions 201 and 202 by the driving amounts $\Delta \theta_1$ and $\Delta \theta_2$ input from the control apparatus 1. FIG. 3 illustrates a block diagram of the position control apparatus 25. A drive angle calculator 26 calculates, by kinematics calculation expressed in Equation (1), target angle driving amounts $\Delta \phi_{1ref}$ and $\Delta \phi_{2ref}$ of the drive sources 211 and 212 required to increase or reduce the angles of the bendable portions by driving amounts $\Delta \theta_1$ and $\Delta \theta_2$.

$$(\Delta \phi_{1ref}, \Delta \phi_{2ref}) = R(\Delta \theta_1, \Delta \theta_2) \quad (1)$$

Position controllers 271 and 272 drive the drive sources 211 and 212 so that the actual angle driving amounts $\Delta \theta_1$ and $\Delta \theta_2$ measured by the encoders 251 and 252 are equal to the target angle driving amounts $\Delta \phi_{1ref}$ and $\Delta \phi_{2ref}$, respectively.

In some exemplary embodiments, the drive sources 211 and 212 are motors, including shaft drives, gear motors, ultrasonic motors, etc. The drive sources are each able to apply drive force to the driving-force transmitting mechanism. One example of this application of a drive force is a motor that, through rotation, causes a wire or cable (the driving-force transmitting mechanism) to move forwards and backwards and thus cause the bendable portion controlled by the driving-force transmitting mechanism to bend. In another embodiment, the drive force is provided through linear motion instead of rotation.

In the exemplary embodiment described in FIG. 2, the second bendable portion 202 has a camera 24 at the distal end thereof, and the camera 24 is arranged such that the viewing direction thereof matches the angle of the distal end of the second bendable portion 202. An image captured by the camera 24 is transmitted through an image transmission cable, and is displayed on the image display device 5 illustrated in FIG. 1. An operator operates the operation-amount input unit 3 while observing the image on the image display device so that the manipulator performs a desired movement. The camera 24 has a zooming function, and the zoom ratio is changed in response to a command from the control apparatus 1.

In some embodiments, the plurality of bendable portions as described herein are formed from the multiple node rings as described in U.S. Pat. Pub. No. 2014/0243592, herein incorporated by reference in its entirety.

1-2 Control System Design

The control apparatus 1 calculates the driving amounts $\Delta\theta_1$ and $\Delta\theta_2$ such that the bending manipulator 2 performs three types of characteristic movements, and such that the amount of movement of the image displayed on the image display device 5 is constant for each type of movement. In this section, first, the relationship between the driving amounts $\Delta\theta_1$ and $\Delta\theta_2$ and the amount of movement of the distal end of the manipulator will be described, and conditions which the driving amounts $\Delta\theta_1$ and $\Delta\theta_2$ need to satisfy to make the amount of movement of the image constant will be derived. Then, details of the three types of characteristic movements will be described, and a method for calculating the driving amounts $\Delta\theta_1$ and $\Delta\theta_2$ for these movements will be derived. Then, the structure of the control apparatus 1 for switching between the movements will be described.

Figures 4A, 4B:
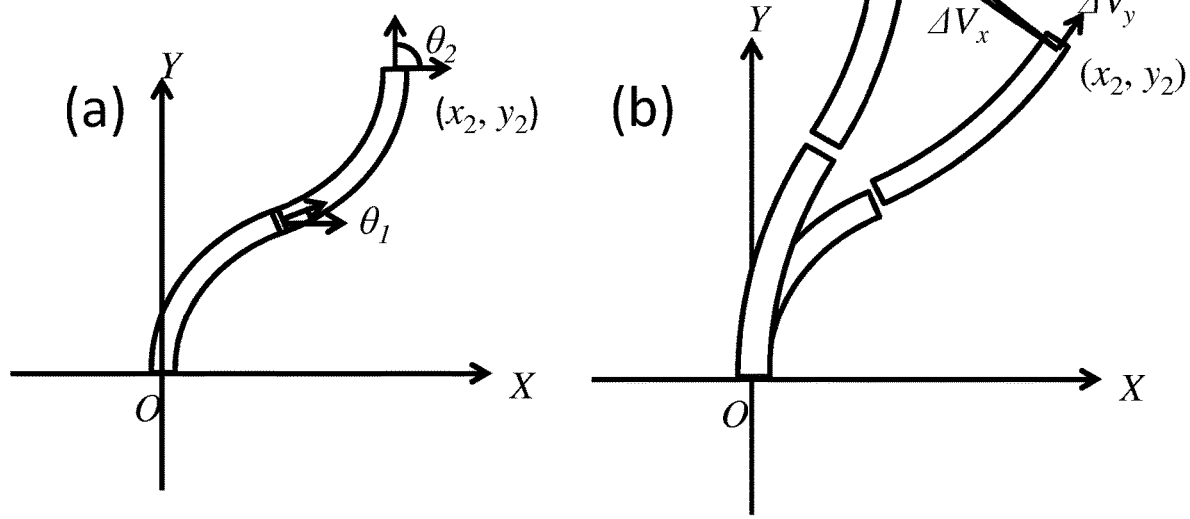
FIGS. 4(a) and 4(b) are graphs showing the coordinate systems of the bendable portions of the manipulator.

FIGS. 4(a) and 4(b) illustrate the coordinate system of the bendable portions. As illustrated in FIG. 4(a), the longitudinal and radial directions of the first bendable portion are respectively defined as a Y-axis and an X-axis. The angle between the X-axis and the distal end of the first bendable portion and the angle between the X-axis and the distal end of the second bendable portion are respectively defined as $\theta_1$ and $\theta_2$. In this case, when the x and y coordinates of the distal end of the second bendable portion are $x_2$ and $y_2$, respectively, the relationship between the coordinates $x_2$ and $y_2$ and the angles $\theta_1$ and $\theta_2$ can be expressed as in Equation (2) based on kinematics calculation.

$$\begin{bmatrix} x_2 \\ y_2 \end{bmatrix} = P(\theta_1, \theta_2) \tag{2}$$

From Equation (2), the coordinates $x_2'$ and $y_2'$ of the distal end of the second bendable portion in the case where the angles of the first and second bendable portions are increased by the driving amounts $\Delta\theta_1$ and $\Delta\theta_2$, respectively, are determined by the following Equation (3).

$$\begin{bmatrix} x_2' \\ y_2' \end{bmatrix} = P(\theta_1 + \Delta\theta_1, \theta_2 + \Delta\theta_2) \tag{3}$$

Thus, the amount of displacement $\Delta V$ of the distal end of the second bendable portion in the case where $\Delta\theta_1$ and $\Delta\theta_2$ are input can be expressed as follows:

$$\Delta V = \begin{bmatrix} x_2' \\ y_2' \end{bmatrix} - \begin{bmatrix} x_2 \\ y_2 \end{bmatrix} = P(\theta_1 + \Delta\theta_1, \theta_2 + \Delta\theta_2) - P(\theta_1, \theta_2) \tag{4}$$

As described above, the operator controls the amount of operation input $\Delta m$ by operating the operation-amount input unit 3 while observing the image captured by the camera disposed at the distal end of the manipulator. Therefore, to improve the operability, it is desirable that the amount of movement of the endoscopic image displayed on the image display device 5 is constant when the operation input $\Delta m$ is constant, irrespective of the position of the manipulator. To achieve this, the first and second bendable portions need to be controlled in accordance with the operation input $\Delta m$ so that three values, which are the angle $\theta_2$ and the coordinates $x_2$ and $y_2$ of the distal end of the second bendable portion, are set to suitable values. However, since the manipulator according to the present embodiment includes only two bendable portions, the number of degrees of freedom of the mechanism is not sufficient. Accordingly, in the present embodiment, the zoom ratio of the camera 24 is changed so as to compensate for the insufficient number of degrees of freedom.

Referring to FIG. 4(b), when a component of the amount of displacement $\Delta V$ of the tip in a direction perpendicular to the viewing direction of the camera 24 is $\Delta V_x$ (hereinafter referred to simply as an amount of movement $\Delta V_x$), $\Delta V_x$ is the amount of movement of the endoscopic image displayed on the image display device 5. When a component of the amount of displacement $\Delta V$ in the viewing direction of the camera 24 is $\Delta V_y$, $\Delta V_y$ is an enlargement or reduction ratio of the endoscopic image. In the present embodiment, the positions of the bendable portions are controlled so that the amount of movement $\Delta V_x$ is proportional to the operation input $\Delta m$. In addition, the zoom ratio of the camera 24 is controlled so as to cancel the influence of the enlargement or reduction of the endoscopic image caused by the movement of the distal end of the manipulator in the direction of $\Delta V_y$.

First, a method for calculating the driving amounts $\Delta\theta_1$ and $\Delta\theta_2$ that make the amount of movement $\Delta V_x$ constant will be described. When the proportionality constant of the amount of movement $\Delta V_x$ with respect to the amount of operation $\Delta m$ is k, Equation (5) is satisfied.

$$\Delta V_x = k\Delta m \tag{5}$$

When the unit vector in the direction of the amount of movement $\Delta V_x$ is $U_x$, $U_x$ can be expressed by using the angle $\theta_2$ as follows:

$$U_x = \begin{bmatrix} \cos\left(\theta_2 + \frac{\pi}{2}\right) \\ \sin\left(\theta_2 + \frac{\pi}{2}\right) \end{bmatrix} \tag{6}$$

Since the amount of movement $\Delta V_x$ can be expressed as the inner product of the amount of displacement $\Delta V$ and the vector $U_x$, the following equation can be derived from Equations (5) and (6).

$$\Delta V_x = \begin{bmatrix} \cos\left(\theta_2 + \frac{\pi}{2}\right) & \sin\left(\theta_2 + \frac{\pi}{2}\right) \end{bmatrix} (P(\theta_1 + \Delta\theta_1, \theta_2 + \Delta\theta_2) - P(\theta_1, \theta_2)) \tag{7}$$

By substituting Equation (5) into Equation (7) and deleting $\Delta V_x$, the following equation is obtained.

$$k\Delta m = \left[ \cos\left(\theta_2 + \frac{\pi}{2}\right) \;\; \sin\left(\theta_2 + \frac{\pi}{2}\right) \right] (P(\theta_1 + \Delta\theta_1, \theta_2 + \Delta\theta_2) - P(\theta_1, \theta_2)) \quad (8)$$

Thus, the amount of movement $\Delta V_x$ can be made constant by calculating the driving amounts $\Delta\theta_1$ and $\Delta\theta_2$ from the operation input $\Delta m$ and the angles $\theta_1$ and $\theta_2$ so as to satisfy Equation (8).

Next, the relationship between the driving amounts $\Delta\theta_1$ and $\Delta\theta_2$ and the amount of movement $\Delta V_y$ will be clarified. When the unit vector in the viewing direction of the camera 24 is $U_y$, $U_y$ can be expressed by using the angle $\theta_2$ as follows:

$$U_y = \begin{bmatrix} \cos\theta_2 \\ \sin\theta_2 \end{bmatrix} \quad (9)$$

The amount of movement $\Delta V_y$ in the viewing direction of the camera 24 is expressed as the inner product of the amount of displacement $\Delta V$ of the tip and the vector $U_y$ as follows:

$$\Delta V_y = [\cos\theta_2 \;\; \sin\theta_2]\{P(\theta_1 + \Delta\theta_1, \theta_2 + \Delta\theta_2) - P(\theta_1, \theta_2)\} \quad (10)$$

By calculating $\Delta V_y$ from Equation (10) and controlling the zoom ratio of the camera 24 so as to cancel the calculated $\Delta V_y$, the size of the observed image displayed on the image display device 5 can be maintained constant even when the distal end of the manipulator is moved.

The further combination of the multiple sections and the prismatic joint allows full control of the position and the direction of the endoscopic view with minimum cascaded multi-section. With the addition of the prismatic joint, the robot can freely position its tip along a planned trajectory or maintain gaze to a disease lesion in two dimensional space Specifically, the tip position can be mapped to the following movement modes by using this full control feature for the position and the direction. Three types of movements that can be performed by the control apparatus 1 will be described with reference to FIGS. 5(a) to 5(c).

Figures 5A, 5B, 5C:
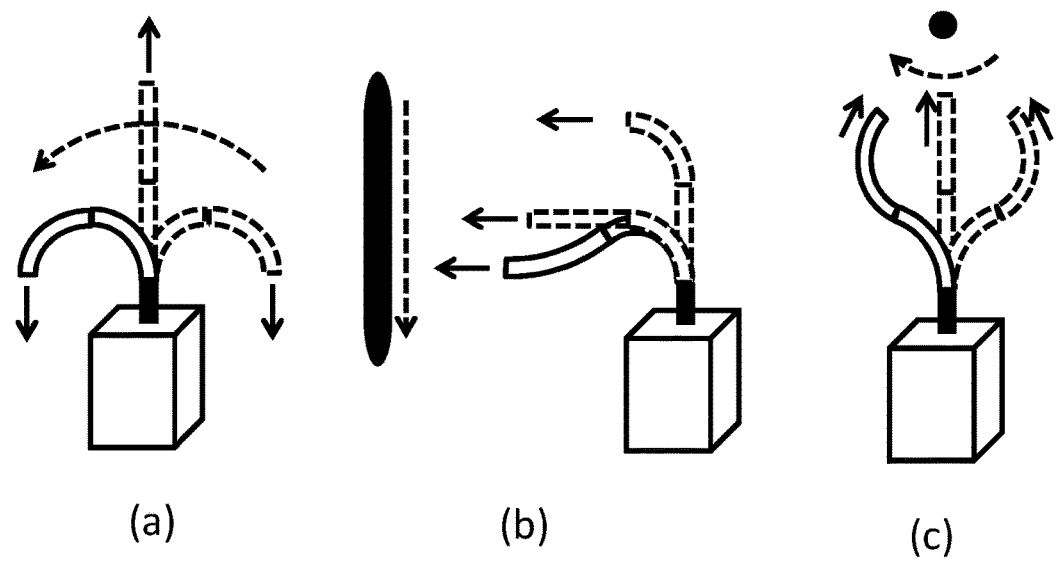
FIGS. 5(a)-5(c) illustrate three types of characteristic movement patterns.

In a first movement illustrated in FIG. 5(a) (hereinafter referred to as a bending movement), the first bendable portion 201 and the second bendable portion 202 are bent in the same direction. With this movement, the position and direction of the distal end of the manipulator can be changed by a large amount. Therefore, the bending movement is suitable for, for example, observing a large area within the body.

In a second movement illustrated in FIG. 5(b) (hereinafter referred to as an angled view movement), the position of the distal end of the manipulator is moved while the angle thereof, that is, the viewing direction of the camera 24, is maintained constant. Therefore, the angled view movement is suitable for, for example, moving an observation unit along a wall surface, such as the stomach wall or intestinal wall that extends at an angle with respect to the insertion direction of the manipulator.

The angled view mode allows orthogonal translational motion along the viewing direction. In this movement mode, the operator will choose the viewing direction and can move the tip along the Cartesian coordinate that directs to the viewing direction. Through this movement mode, the viewing angle is fixed to the one direction. Therefore, this movement mode is useful to scan a wide range of area that includes the targeted lesions.

The angled view mode is described in more detail in Kato, T. et al., "Tendon-Driven Continuum Robot for Endoscopic Surgery: Preclinical Development and Validation of a Tension Propagation Model," *Mechatronics, IEEE/ASME Transactions on*, vol. PP, no. 99, pp. 1,12 herein incorporated by reference in its entirety. See also Kato, T.; Okumura, I.; Kose, H.; Takagi, K.; Hata, N., "Extended kinematic mapping of tendon-driven continuum robot for neuroendoscopy," Intelligent Robots and Systems (IROS 2014), 2014 IEEE/RSJ International Conference on, vol., no., pp. 1997, 2000, 14-18 Sep. 2014, which is also herein incorporated by reference in its entirety.

In a third movement illustrated in FIG. 5(c) (hereinafter referred to as remote center movement), the position and angle of the distal end of the second bendable portion are changed so that the line of sight of the camera 24 constantly passes through a single distant point. Therefore, the remote center movement is suitable in the case where, for example, a portion that cannot be viewed from the front, such as the back side of a folded portion of the intestinal wall, is viewed from the back side.

In some embodiments, a remote center of the motion movement mode allows the manipulator to be pivoted around the targeted lesion. By using the combination of motions between bending sections and the translation motion, the tip can turn around the lesion with an identical distance between the tip and the target while the tip keeps to be directed to the lesion. The operator can choose this distance to have an optimal view or optimal access of the tools to the lesion. Therefore, this movement mode is particularly useful to investigate and access the lesion from different angles.

Next, a method for calculating the driving amounts $\Delta\theta_1$ and $\Delta\theta_2$ for performing the bending movement, the angled view movement, and the remote center movement will be described. In the bending movement according to the present embodiment, the first and second bendable portions are driven so that the ratio between the driving amounts $\Delta\theta_1$ and $\Delta\theta_2$ is constant. In this case, the driving amounts $\Delta\theta_1$ and $\Delta\theta_2$ satisfy Equation (11).

$$\Delta\theta_1 = c\Delta\theta_2 \quad (11)$$

Therefore, the driving amounts $\Delta\theta_1$ and $\Delta\theta_2$ for the bending movement can be calculated by solving Equations (8) and (11) as simultaneous equations. In the angled view movement, the driving operation is performed so that the angle $\theta_2$ of the distal end of the second bendable portion is maintained constant. Accordingly, the driving amount $\Delta\theta_2$ is constantly set to 0 as in expressed Equation (12).

$$\Delta\theta_2 = 0 \quad (12)$$

The driving amount $\Delta\theta_1$ for performing the angled view movement can be calculated by substituting Equation (12) into Equation (8). In the remote center movement, as described above, the line of sight of the camera 24 is moved around a single distant point. The straight line that represents the line of sight of the camera 24 after the movement can be can be expressed by using the coordinates $x_2'$ and $y_2'$ and the angle $\theta_2$ of the distal end of the second bendable portion as follows:

$$\tan(\theta_2 + \Delta\theta_2) = \frac{y - y_2'}{x - x_2'} \quad (13)$$

When the x and y coordinates of the center of the remote center movement are $x_c$ and $y_c$, respectively, the straight line expressed by Equation (13) passes through the center $(x_c, y_c)$ when Equation (14) is satisfied.

$$\tan(\theta_2 + \Delta\theta_2) = \frac{y_c - y_2'}{x_c - x_2'} \quad (14)$$

By deleting the coordinates $x_2'$ and $y_2'$ from Equation (14) by using Equation (3) and solving the resulting equation and Equation (8) as simultaneous equations, the driving amounts $\Delta\theta_1$ and $\Delta\theta_2$ for performing the remote center movement can be calculated.

Figure 6:
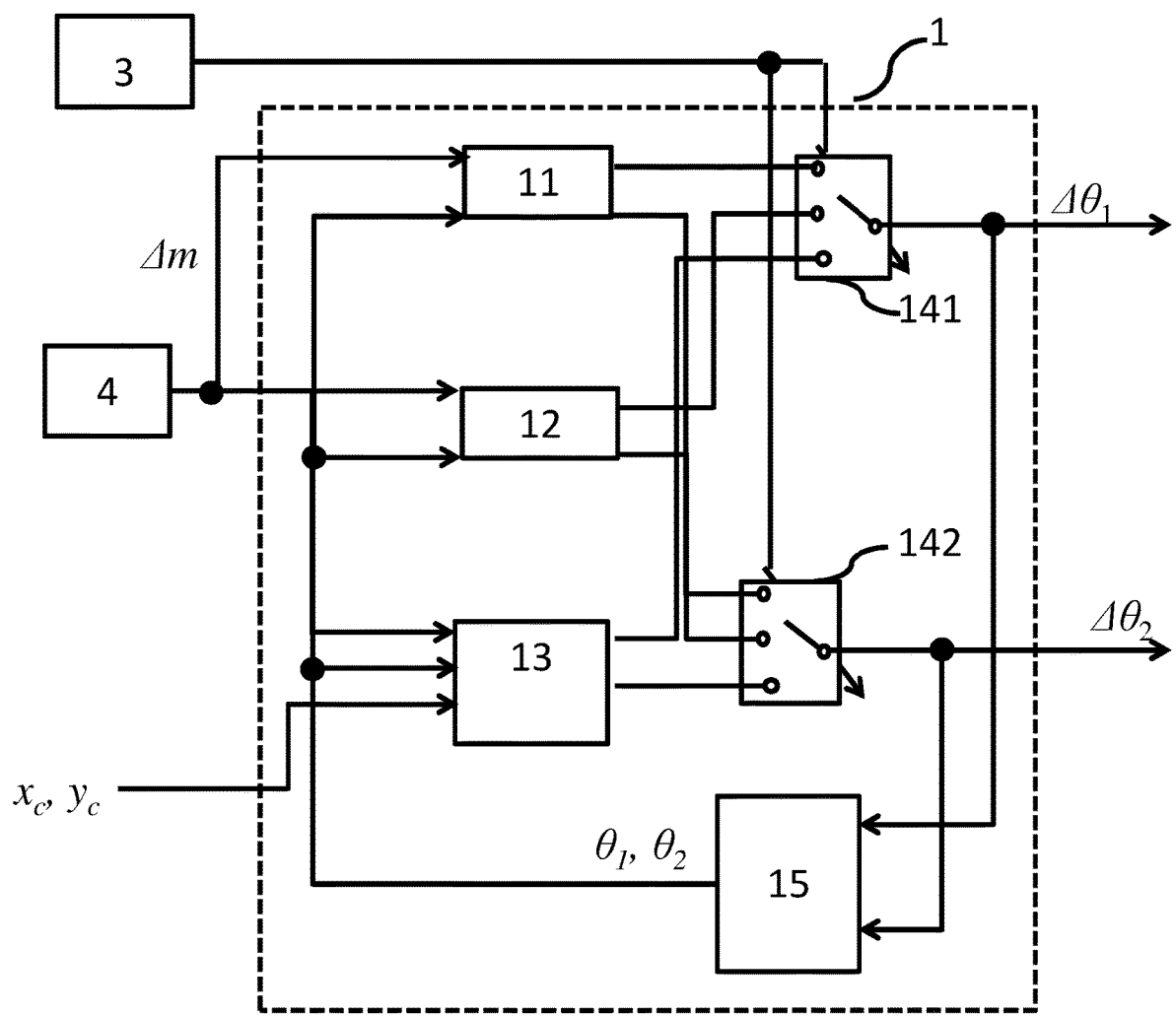
FIG. 6 is a block diagram of a manipulator control apparatus according to a first embodiment.

A method by which the control apparatus 1 switches between the bending movement, the angled view movement, and the remote center movement will now be described. This switching function is used in the case where, for example, the bending movement is performed to find an observation target from a wide area, and then the angled view movement and/or the remote center movement is carried out to perform detailed observation. FIG. 6 is a block diagram of the control apparatus 1. The control apparatus 1 includes a first driving-amount calculator 11, a second driving-amount calculator 12, a third driving-amount calculator 13, movement-mode selecting units 141 and 142, and an integrator 15. The first driving-amount calculator 11 receives the amount of operation $\Delta m$ and the angles $\theta_1$ and $\theta_2$, and calculates the driving amounts for the bending movement by using Equations (8) and (11). Similarly, the second driving-amount calculator 12 calculates the driving amounts for the angled view movement by using Equations (8) and (12). The third driving-amount calculator 13 receives the amount of operation $\Delta m$ and the coordinates $x_c$ and $y_c$, and calculates the driving amounts for the remote center movement by using Equations (3), (8), and (14). The drive-mode selecting units 141 and 142 select the driving amounts output from the first, second, or third driving-amount calculator, and output the selected driving amounts. The integrator 15 calculates the angles $\theta_1$ and $\theta_2$ by integrating the driving amounts $\Delta\theta_1$ and $\Delta\theta_2$.

Second Embodiment 2-1 Control System Design

According to the first embodiment, the control apparatus 1 calculates $\Delta\theta_1$ and $\Delta\theta_2$ so as to make the amount of movement $\Delta V_x$ constant based on the kinematics calculation expressed in Equations (1) and (2). However, in the actual manipulator, owing to stretching of the wires, looseness of the mechanism, or wear, the angles and positions of the distal ends of the bendable portions determined by the kinematics calculation include errors. Owing to the errors, even when a constant amount of operation $\Delta m$ is input, the amount of movement $\Delta V_x$ may vary by a large amount and the operability may be degraded. Accordingly, in this embodiment, first, the reason why the amount of movement $\Delta V_x$ varies by a large amount when the result of the kinematics calculation includes an error will be described in detail. Then, a control system that calculates the driving amounts $\Delta\theta_1$ and $\Delta\theta_2$ with which the variation can be reduced will be designed.

2-1-1

Figure 7:
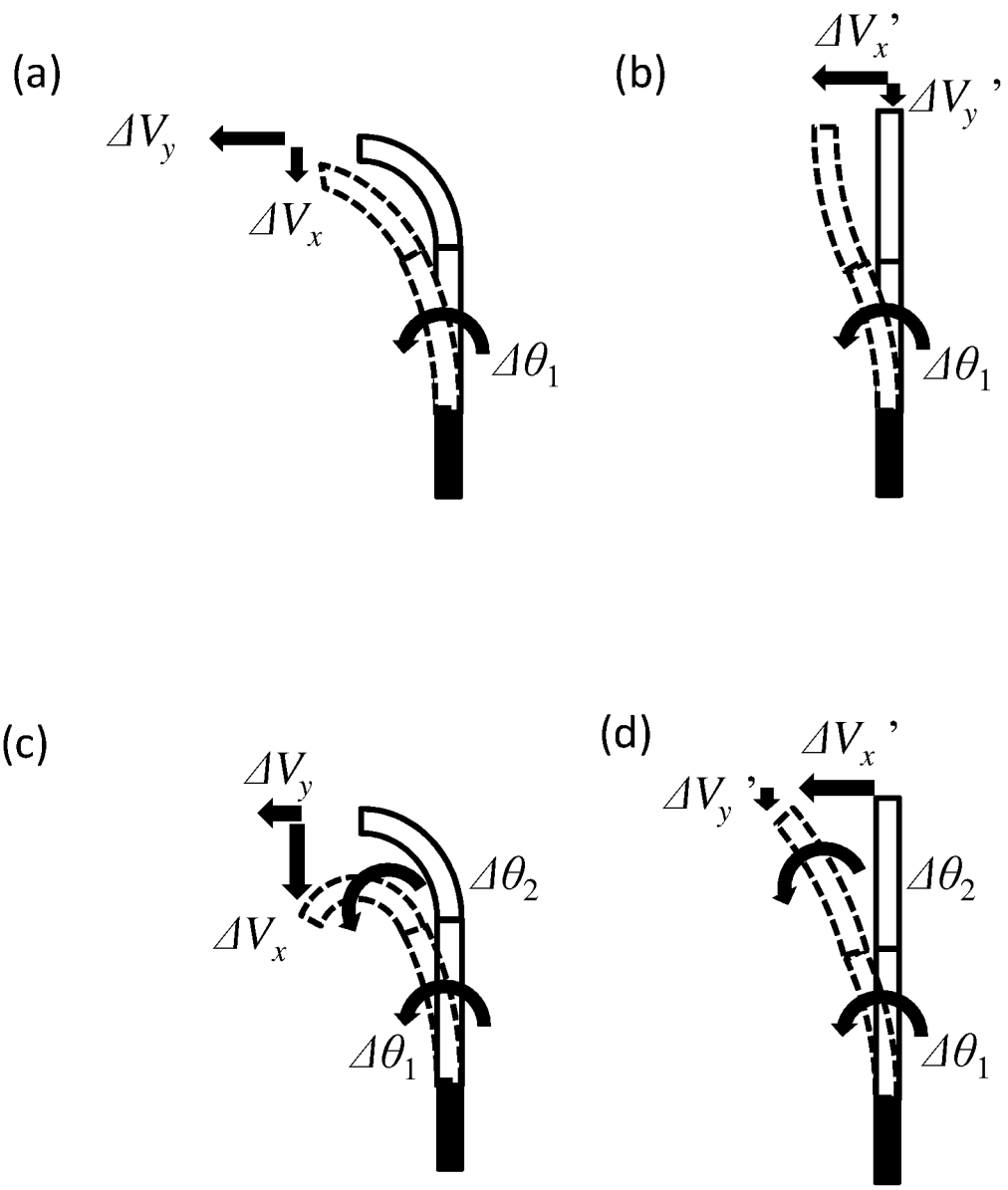
FIGS. 7(a)-7(d) illustrate the relationship between the bending angles of the manipulator and the position of the distal end of the manipulator.

As is clear from Equation (7), the amount of movement $\Delta V_x$ that corresponds to the driving amounts $\Delta\theta_1$ and $\Delta\theta_2$ depends on the angles $\theta_1$ and $\theta_2$ (this characteristic is hereinafter referred to as angle dependency). The control apparatus 1 of the first embodiment calculates the driving amounts $\Delta\theta_1$ and $\Delta\theta_2$ so as to compensate for the angle dependency by the kinematics calculation expressed in Equation (8). However, when the kinematics calculation includes a large error, the angle dependency is amplified instead of being compensated for. For example, assume that the angled view movement is performed from the state in which the first bendable portion is straight as illustrated in FIGS. 7(a) and 7(b). In this case, when only the first bendable portion is driven by the driving amount $\Delta\theta_1$ while the angle of the second bendable portion is maintained constant, the distal end of the second bendable portion is moved in the negative X-axis direction. In the case where the second bendable portion is bent as illustrated in FIG. 7(a), the amount of movement $\Delta V_y$ in the viewing direction of the camera is large, and the amount of movement $\Delta V_x$ in the direction perpendicular to the viewing direction is small. In contrast, in the case where the second bendable portion is straight as illustrated in FIG. 7(b), the amount of movement $\Delta V_x$ in the direction perpendicular to the viewing direction is large. Therefore, the driving amount $\Delta\theta_1$ for causing the amount of movement $\Delta V_x$ to satisfy Equation (5) is greater in the case where the manipulator is in the position illustrated in FIG. 7(a) than in the case where the manipulator is in the position illustrated in FIG. 7(b). As a result, the amount of movement $\Delta V_x$ is increased. For example, assume that the actual position of the manipulator is that illustrated in FIG. 7(b), but the driving amount $\Delta\theta_1$ for the position illustrated in FIG. 7(a) is calculated due to the error in the kinematics calculation. As described above, when the manipulator is in the position illustrated in FIG. 7(b), the amount of movement $\Delta V_x$ is large even when the driving amount $\Delta\theta_1$ is small. In addition, the driving amount $\Delta\theta_1$ calculated on the assumption that the manipulator is in the position illustrated in FIG. 7(a) is greater than the driving amount required to achieve the amount of movement $\Delta V_x$ when the manipulator is in the position illustrated in FIG. 7(b). Therefore, the actual amount of movement of the distal end portion is excessively large.

Next, a discontinuous change in the amount of movement $\Delta V_x$ that occurs when the movement mode is switched will be described. The discontinuous change occurs due to the differences in angle dependency between the movement modes. For example, to show that the angle dependency of the bending movement is smaller than that of the angled view movement, a case where the bending movement is performed from the state in which the first bendable portion is straight as illustrated in FIG. 7(c) will be described. In the bending movement, the first and second bendable portions are bent in the same direction. When the second bendable portion is driven, the distal end of the manipulator is moved in the direction of $\Delta V_x$. Therefore, as illustrated in FIG. 7(c), even when the amount of movement in the direction of $\Delta V_x$ caused by the driving operation of the first bendable portion is small, this can be compensated for by the diving operation of the second bendable portion. Accordingly, the driving amounts $\Delta\theta_1$ and $\Delta\theta_2$ that satisfy Equation (5) do not vary by a large amount irrespective of the angles $\theta_1$ and $\theta_2$ of the bendable portions. In contrast, as described above, the angle dependency of the angled view movement is large. Therefore, when the driving amounts $\Delta\theta_1$ and $\Delta\theta_2$ calculated on the assumption that the manipulator is in a position different from the actual position are input, the amount of movement of the tip varies by a large amount. Due to the difference in angle dependency, the amount of movement of the tip varies discontinuously when the movement mode is switched. For example, assume that the movement mode is switched from the bending movement to the angled view movement. In addition, assume that actual manipulator is in the position such that the second bendable portion is straight, as illustrated in FIGS. 7(b) and 7(d), but the driving amounts are calculated on the assumption that the second bendable portion is bent as illustrated in FIGS. 7(a) and 7(c). In this case, although the movement speed of the endoscopic image is constant during the bending movement since the amount of movement $\Delta V_x$ does not vary by a large amount, the movement speed suddenly changes when the movement mode is switched to the angled view movement. Thus, the operability is degraded.

2-1-2

As described in the previous section, although the control apparatus 1 according to the first embodiment calculates the driving amounts $\Delta\theta_1$ and $\Delta\theta_2$ so as to compensate for the angle dependency, there is a risk that the variation in the amount of movement $\Delta V_x$ of the distal end of the second bendable portion will be amplified due to the error in the kinematics calculation. Therefore, in the present embodiment, the first, second, and third driving-amount calculators are designed so that the driving amounts $\Delta\theta_1$ and $\Delta\theta_2$ will be constant irrespective of the angles $\theta_1$ and $\theta_2$. With the control method according to the present embodiment, since the angle dependency cannot be compensated for, the amount of movement $\Delta V_x$ cannot be made constant even when the operation input $\Delta m$ is constant. However, variation in the amount of movement $\Delta V_x$ can be reduced even when the kinematics calculation has a large error.

Figure 8:
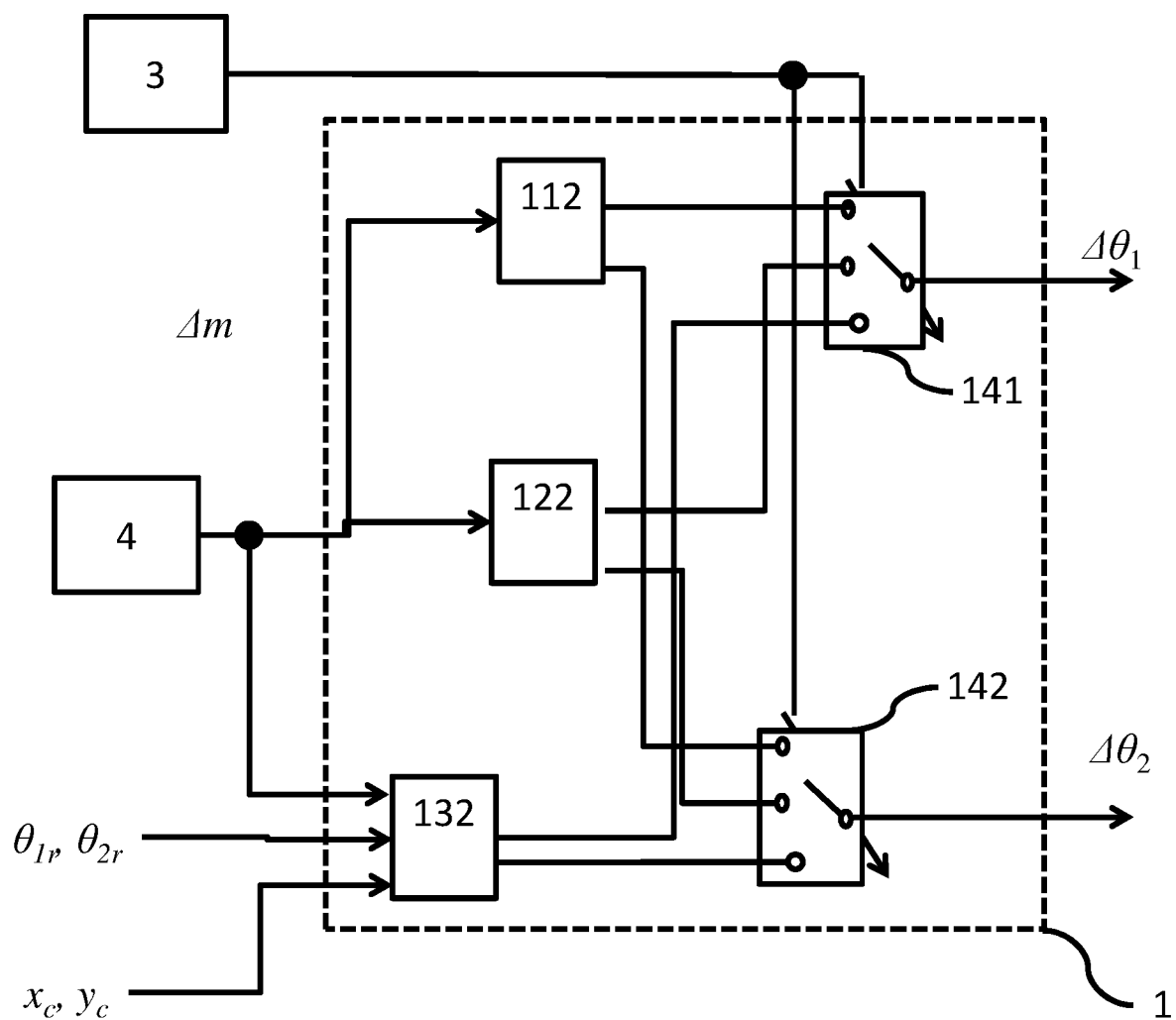
FIG. 8 is a block diagram of a manipulator control apparatus according to a second embodiment.
Figure 9A:
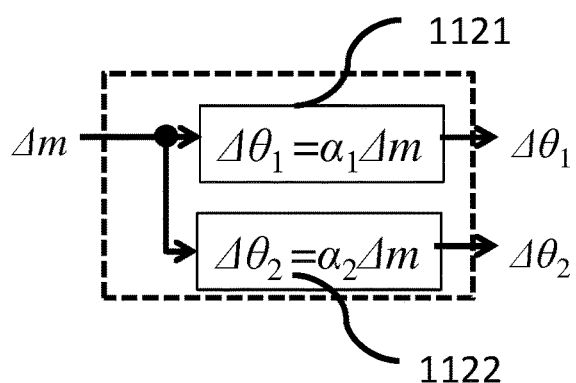
FIGS. 9(a)-9(c) are block diagrams of driving-amount calculators according to the second embodiment.
Figure 9B:
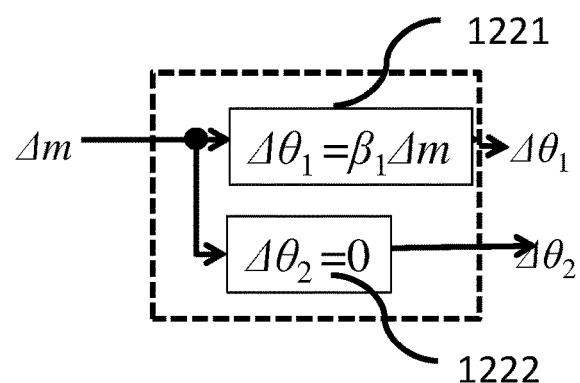
Figure 9C:
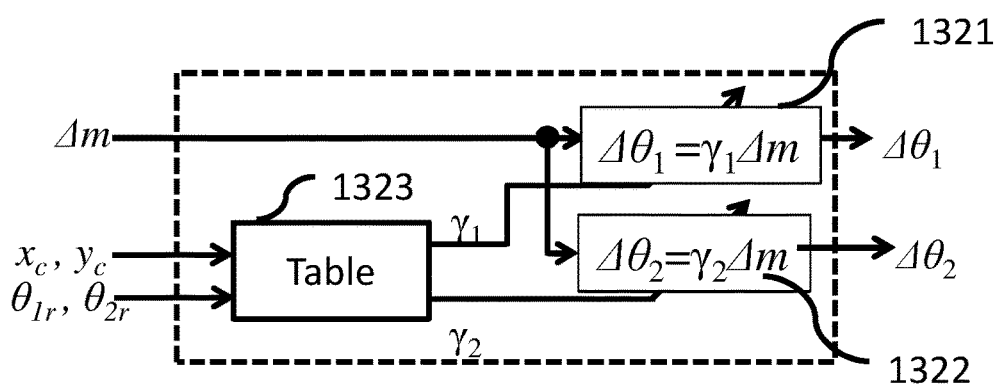

FIG. 8 is a block diagram of a control apparatus 1 according to the present embodiment. Driving-amount calculators 112, 122, and 132 included in the control apparatus 1 differ from the corresponding calculators in the first embodiment in that the driving amounts are calculated without using the angles $\theta_1$ and $\theta_2$ of the first and second bendable portions. FIGS. 9(a) to 9(c) are block diagrams of the driving-amount calculators 112, 122, and 132, respectively. The driving-amount calculators include amplifiers 1121, 1122, 1221, 1222, 1321, and 1322 that calculate the driving amounts of the first and second bendable portions by multiplying the operation input $\Delta m$ by constants. When amplification factors of the amplifiers are appropriately set, the bending movement, the angled view movement, and the remote center movement can be performed. In the present embodiment, the amplification factors $\alpha_1$ and $\alpha_2$ of the amplifiers 1121 and 1122 of the first driving-amount calculator 112 are set to constants having the same sign. Accordingly, the first and second bendable portions are driven in the same direction at constant rates, so that the bending movement can be performed in which the distal end of the second bendable portion is moved by a large amount. In addition, an amplification factor $\beta_1$ of the amplifier 1221 of the second driving-amount calculator 122 is set to a constant that is not 0, and an amplification factor of the amplifier 1222 is set to 0. Since the driving amount $\Delta\theta_2$ is constantly set to 0, the angle $\theta_2$ does not change from the value at the time when the movement mode was switched to the angled view movement, and is maintained constant. In this embodiment, the third driving-amount calculator 132 receives a table 1323 from a host apparatus, which includes the coordinates $x_c$ and $y_c$ of the observation center and angles $\theta_{1r}$ and $\theta_{2r}$ of the first and second bendable portions at the time when the movement mode was switched to the remote center movement. The table 1323 outputs amplification factors $\gamma_1$ and $\gamma_2$ for the remote center movement at angles close to the angles $\theta_{1r}$ and $\theta_{2r}$ on the basis of the input signals.

2-2 Simulation

Figure 10:
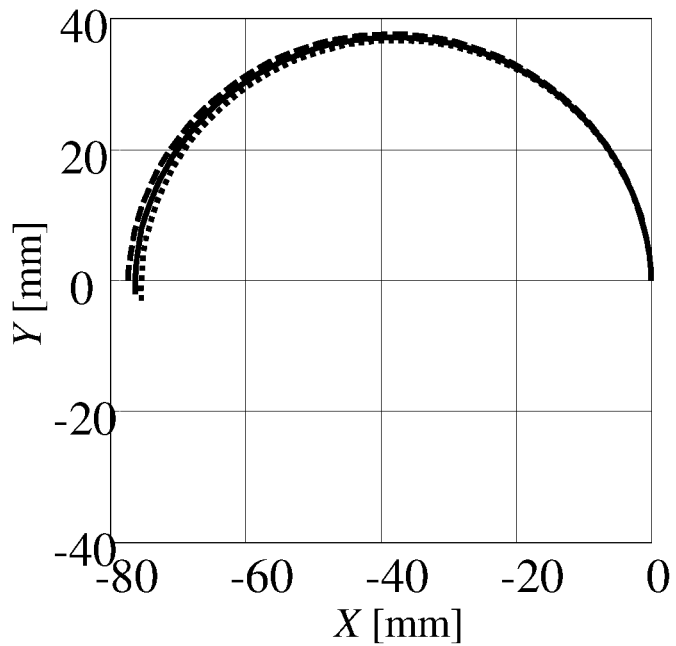
FIG. 10 is a graph showing a simulation result according to the second embodiment.

In this section, a simulation result that shows that the variation in the amount of movement $\Delta V_x$ can be reduced by the control system described in the previous section will be described. In this section, for example, it is assumed that the angled view movement and switching between the angled view movement and the bending movement are performed around the position shown by the solid line in FIG. 10 in which the angles $\theta_1$ and $\theta_2$ are $\pi$ rad and $2\pi$ rad, respectively (hereinafter referred to as a turn-around position). In the simulation, in each of the angled view movement and the bending movement, the position shown by the dashed line in FIG. 10 is set as the initial position, and the driving operation is performed such that the position is changed to the turn-around position at 20 sec, and to the position shown by the dotted line at 40 sec. The constant kin Equation (5) is set to 1, the amount of movement $\Delta V_x$ is set to 0.05 mm/sec, and the amplification factors $\alpha_1$, $\alpha_2$, and $\beta_1$ are set to $1.0\times10^{-3}$, $2.0\times10^{-3}$, and $1.2\times10^{-2}$, respectively. In the simulation, it is assumed that the error in the position is due to detection errors of the angles of the distal ends of the first and second bendable portions, and the angle errors are $-\pi/30$ rad and $\pi/30$ rad.

Figures 11A, 11B:
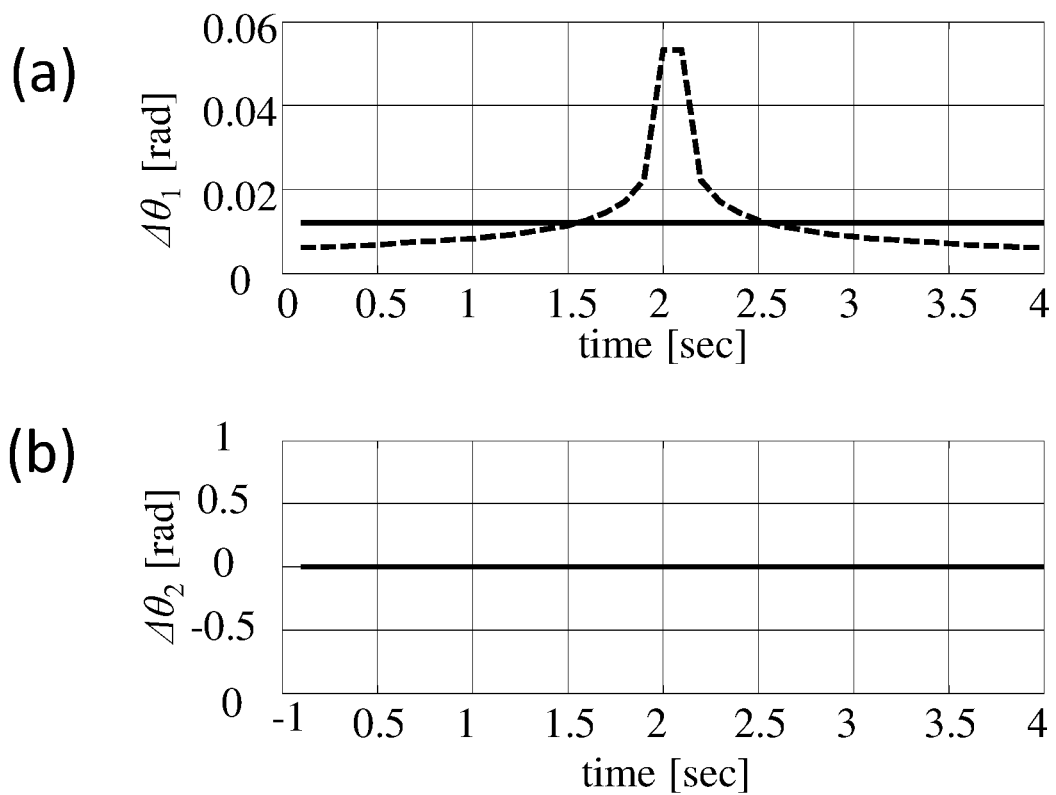
FIGS. 11(a) and 11(b) are graphs showing a simulation result according to the second embodiment.

First, it will be described how the variation in the amount of movement $\Delta V_x$ can be reduced by calculating the driving amounts for the angled view movement by the control method according to the present embodiment. FIGS. 11(a) and 11(b) show the driving amounts $\Delta\theta_1$ and $\Delta\theta_2$ in the angled view movement. In FIGS. 11(a) and 11(b), the solid lines show the driving amounts calculated by the method according to the present embodiment (hereinafter referred to as constant driving amounts), and the dashed lines show the driving amounts calculated by the method based on kinematics described in the first embodiment (hereinafter referred to as variable driving amounts). This also applies to the following drawings. As is clear from the dashed line in FIG. 11(a), the variable driving amount for the first bendable portion is increased by a large amount at 20 sec. This is because, as described above, the angle dependency is compensated for. In contrast, the constant driving amount shown by the solid line is constant. Since the second bendable portion is not driven in the angled view movement, as shown by the dashed and solid lines in FIG. 11(b), the driving amount $\Delta\theta_2$ is maintained at 0.

FIG. 12 shows the amount of movement $\Delta V_x$ in the angled view movement. As is clear from the solid and dashed lines in FIG. 12, in each of the cases where the constant driving amounts and the variable driving amounts are input into the device, the amount of movement $\Delta V_x$ is not constant. However, the inclination of the solid line is constant, which shows that the amount of movement $\Delta V_x$ changes at a constant rate when the constant driving amounts are input. Accordingly, the operator can easily maintain the movement speed of the tip constant by reducing the operation input $\Delta m$ in accordance with the increase in the amount of movement $\Delta V_x$ while observing the displayed endoscopic image. Therefore, in embodiments where an endoscope provides a real time image, that image can have a constant image.

As is clear from the dashed line in FIG. 12, when a simulation including variable driving amounts are input, the amount of movement $\Delta V_x$ is suddenly increased at the time around 2.0 sec. This is due to a large driving amount $\Delta\theta_1$ is input to the first bendable portion, as shown by the dashed line in FIG. 11(a), even though the actual position is different from the turn-around position. Since the operator cannot predict when the sudden change in the amount of movement $\Delta V_x$ will occur, it is difficult for the operator to change the operation input Δm so as to maintain the movement speed of the end of the tip constant on the basis of the displayed image. Thus, the operability may be degraded in this mode.

Next, it will be described how the discontinuous change in the movement speed of the tip due to switching of the movement mode can be suppressed by using the control apparatus according to the present embodiment. FIGS. 13(a) and 13(b) show the driving amounts $\Delta\theta_1$ and $\Delta\theta_2$ in the case where the movement mode is switched from the bending movement to the angled view movement at 20 sec. As is clear from the solid and dashed lines in FIGS. 13(a) and 13(b), the driving amounts $\Delta\theta_1$ and $\Delta\theta_2$ are substantially constant in the period from 0 sec to 20 sec in which the bending movement is performed. This is because, as described above, the angle dependency of the bending movement is small. In addition, it is clear from the dashed line in FIG. 13(a) that, similar to FIG. 11(a), the variable driving amount increases at 20 sec at which the angled view movement is performed in the turn-around position. Therefore, the driving amount $\Delta\theta_1$ varies discontinuously in the period around 20 sec. In contrast, it is clear from the solid line in FIG. 13(a) that a change in the constant driving amount around 20 sec is smaller than that in the variable driving amount.

Figure 14:
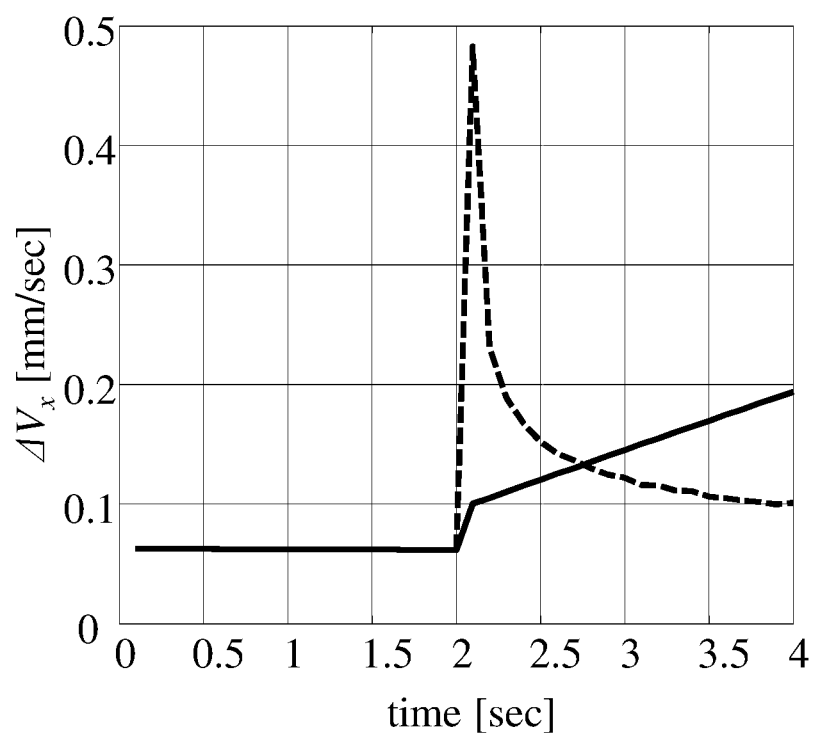
FIG. 14 is a graph showing a simulation result according to the second embodiment.

FIG. 14 shows the amount of movement $\Delta V_x$ in the case where the driving amounts shown in FIGS. 13(a) and 13(b) are input when the angle errors are present. As is clear from the solid line in FIG. 14, when the constant driving amounts are input, the amount of movement $\Delta V_x$ does not change by a large amount even at 20 sec at which the movement mode is switched. Therefore, by using the control apparatus according to the present embodiment, even when the angle errors are present, the movement speed of the tip can be prevented from changing suddenly at the time of switching of the movement mode. Therefore, the operability is not degraded. In contrast, it is clear from the dashed line in FIG. 14 that when the variable driving amounts are input, the amount of movement $\Delta V_x$ is discontinuously and suddenly increased at 20 sec. Accordingly, even though the operation input Δm is constant, the movement speed of the endoscopic image varies by a large amount when the movement mode is switched. Thus, the operability is degraded.

One particularly advantageous feature of the control apparatus and endoscopes as described herein is their ease of use. During surgery, a doctor or other clinician has to manipulate and often control the patient, multiple tools, sterilizing equipment, and other devices during the surgical procedure. Thus, simplification of the controls in the endoscopic device such that it can be controlled with one hand or simply with movement along one dimension is particularly advantageous. The ability to select a movement-mode and then, using a joystick that may only have movement in a single direction (up and down or side to side), a touch screen, a foot pedal, or voice-operated control (for example, calling out a numerical unit) allows for simplified movements that may be easier to learn but still allows for significant flexibility in how the target image is vied since the operator can select one of several different movement-mode depending on what the target is and what needs to be done.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

What is claimed is:

1. A control apparatus for a manipulator including a plurality of bendable portions, the control apparatus comprising:
    a plurality of driving-force transmitting mechanisms that are connected to the bendable portions and that bend the manipulator;
    a plurality of drive sources that apply drive forces to the driving-force transmitting mechanisms;
    an operation-amount input unit that generates an operation signal based on an amount of operation of an operating portion, wherein the operation-amount input unit is used while advancing or retracting the manipulator and the amount of operation of the operating portion is proportional to the amount of operation of the manipulator;
    a movement-mode input unit that selects one of a plurality of movement modes, wherein a movement of at least one of the plurality of movement modes is predetermined and disproportional to the amount of operation of the manipulator; and
    a calculating device that calculates and outputs driving amounts to be applied to the drive sources on the basis of the operation signal, the driving amounts corresponding to the movement modes,
    wherein the calculating device includes
        a plurality of driving-amount calculators, and
        the movement-mode selecting unit that outputs the driving amounts output by one of the driving-amount calculators on the basis of an input signal from movement-mode input unit.

2. The control apparatus according to claim 1, wherein one of the driving-amount calculators calculates the driving amounts so that the bendable portions are bent in the same direction.

3. The control apparatus according to claim 2, wherein the one of the driving-amount calculators includes a plurality of first amplifiers that calculate the driving amounts by amplifying the operation signal.

4. The control apparatus according to claim 1, wherein one of the driving-amount calculators calculates the driving amounts such that an angle of a distal end of at least one of the bendable portions is constant.

5. The control apparatus according to claim 4, wherein the one of the driving-amount calculators includes a second amplifier that calculates a corresponding one of the driving amounts by amplifying the operation signal, and
    wherein the second amplifier corresponds to the at least one of the bendable portions having the distal end whose angle is constant, and an amplification factor of the second amplifier is set to zero.

6. The control apparatus according to claim 1, wherein one of the driving-amount calculators receives observation-target coordinates and calculates the driving amounts such that a straight line that extends in a longitudinal direction from the most distal bendable portion of the manipulator passes through a position specified by the coordinates.

7. The control apparatus according to claim 6,
    wherein the one of the driving-amount calculators includes
        a plurality of third amplifiers that calculate the driving amounts by amplifying the operation signal, and
        a storage section that receives a signal of the observation-target coordinates and outputs third amplification factors of the third amplifiers, and
    wherein the driving amounts are calculated by amplifying the operation signal by the third amplification factors.

8. The control apparatus according to claim 1, wherein the plurality of movement modes comprises a bending movement mode, an angled view movement mode, and a remote center movement mode.

9. A manipulator system comprising:
   a manipulator comprising a plurality of bendable portions and a plurality of driving-force transmitting mechanisms that are connected to the bendable portions and that bend the manipulator; and
   a control apparatus comprising:
      a plurality of drive sources that apply drive forces to the driving-force transmitting mechanisms;
      an operation-amount input unit that generates an operation signal based on an amount of operation of an operating portion, wherein the operation-amount input unit is used while advancing or retracting the manipulator;
      a movement-mode input unit that selects one of a plurality of movement modes, wherein a movement of at least one of the plurality of movement modes is predetermined and disproportional to the amount of operation of the manipulator; and
      a calculating device that calculates and outputs driving amounts to be applied to the drive sources on the basis of the operation signal, the driving amounts corresponding to the movement modes,
   wherein the calculating device includes
      a plurality of driving-amount calculators, and
      the movement-mode selecting unit that outputs the driving amounts output by one of the driving-amount calculators on the basis of an input signal from movement-mode input unit.

10. The manipulator system of claim 9, wherein the manipulator is adapted for insertion of one or more endoscopic tools there though.

11. The manipulator system of claim 9, wherein the plurality of movement modes comprises a bending movement mode, an angled view movement mode, and a remote center movement mode.

12. An endoscopic system having a simplified control comprising:
   a manipulator comprising a plurality of bendable portions and having at least three degrees of freedom;
   a control apparatus for controlling movement of the manipulator through the at least three degrees of freedom having two input units comprising:
      a movement-mode input unit adapted for selecting one of 2, 3, 4, 5, or 6 movement modes, wherein a movement of at least one of the 2, 3, 4, 5, or 6 movement modes is predetermined and disproportional to the amount of operation of the manipulator; and
      an operation-amount input unit adapted for generating an operation signal based on a linear parameter from an operator, wherein the operation-amount input unit is used while advancing or retracting the manipulator; and
      a calculating device configured to calculate driving amounts for driving the manipulator in a motion through at least one of the at least three degrees of freedom.

13. The endoscopic system of claim 12, wherein the at least three degrees of freedom of the manipulator comprises two bending motions and a translational motion.

14. The endoscopic system of claim 12, wherein the operation-amount input unit inputs a linear parameter.

15. The endoscopic system of claim 12, wherein the calculating device calculates at least three driving amounts for at least three degrees of freedom of the manipulator.

* * * * *